United States Patent
Muntz et al.

(10) Patent No.: US 7,690,241 B2
(45) Date of Patent: Apr. 6, 2010

(54) PRE-CONCENTRATOR FOR TRACE GAS ANALYSIS

(75) Inventors: Eric P. Muntz, Pasadena, CA (US); Marcus P. Young, Los Angeles, CA (US); Yen-Lin Han, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 621 days.

(21) Appl. No.: 11/552,360

(22) Filed: Oct. 24, 2006

(65) Prior Publication Data

US 2008/0178658 A1 Jul. 31, 2008

Related U.S. Application Data

(60) Provisional application No. 60/729,679, filed on Oct. 24, 2005.

(51) Int. Cl.
  *G01N 7/00* (2006.01)
(52) U.S. Cl. ...................................... 73/31.07
(58) Field of Classification Search ................. 73/31.07; 96/4
  See application file for complete search history.

(56) References Cited

U.S. PATENT DOCUMENTS

| | | | |
|---|---|---|---|
| 4,284,418 A * | 8/1981 | Andres | 95/32 |
| 4,293,316 A * | 10/1981 | Block | 95/50 |
| 4,767,524 A * | 8/1988 | Yeh et al. | 209/143 |
| 5,491,337 A * | 2/1996 | Jenkins et al. | 250/287 |
| 6,386,015 B1 * | 5/2002 | Rader et al. | 73/31.05 |
| 7,141,786 B2 * | 11/2006 | McGann et al. | 250/287 |
| 7,178,380 B2 * | 2/2007 | Shekarriz et al. | 73/28.04 |
| 2006/0162424 A1 * | 7/2006 | Shekarriz et al. | 73/28.06 |
| 2008/0078289 A1 * | 4/2008 | Sergi et al. | 95/25 |

* cited by examiner

*Primary Examiner*—Hezron Williams
*Assistant Examiner*—Gunnar J Gissel
(74) *Attorney, Agent, or Firm*—McDermott Will & Emery LLP

(57) ABSTRACT

A continuously operating pre-concentrator for trace gas analysis includes a flow channel, a pumping chamber, and a separation membrane between the flow channel and the pumping chamber. The flow channel has a width that decreases from the inlet to the outlet in such a way that the trace gas and the carrier gas maintain a substantially constant flow speed through the flow channel. The separation membrane is configured to allow preferential removal of molecules of the carrier gas from the flow channel, as the gas sample flows from the inlet to the outlet, thereby increasing concentration of the trace gas in the gas sample. The separation membrane includes a substantially non-adsorbing material that allows the gas sample to flow substantially continuously through the flow channel, so that a variation in concentration of the trace gas can be detected in substantial real time.

24 Claims, 3 Drawing Sheets

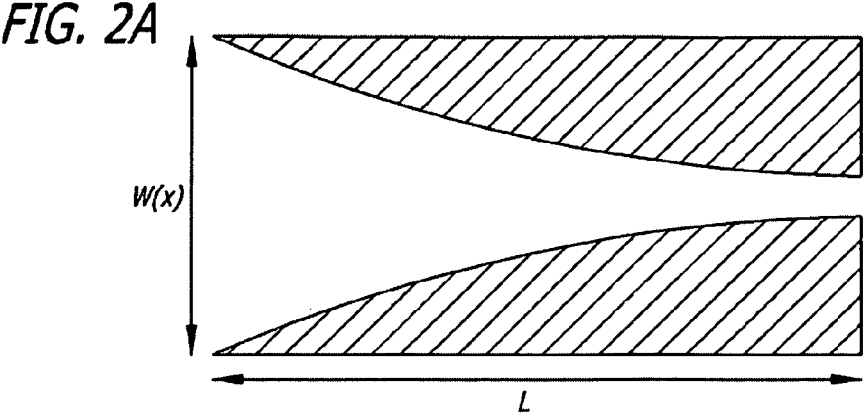
FIG. 2A
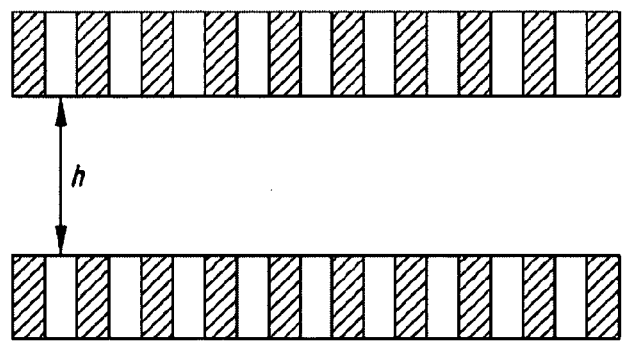
FIG. 2B
FIG. 3
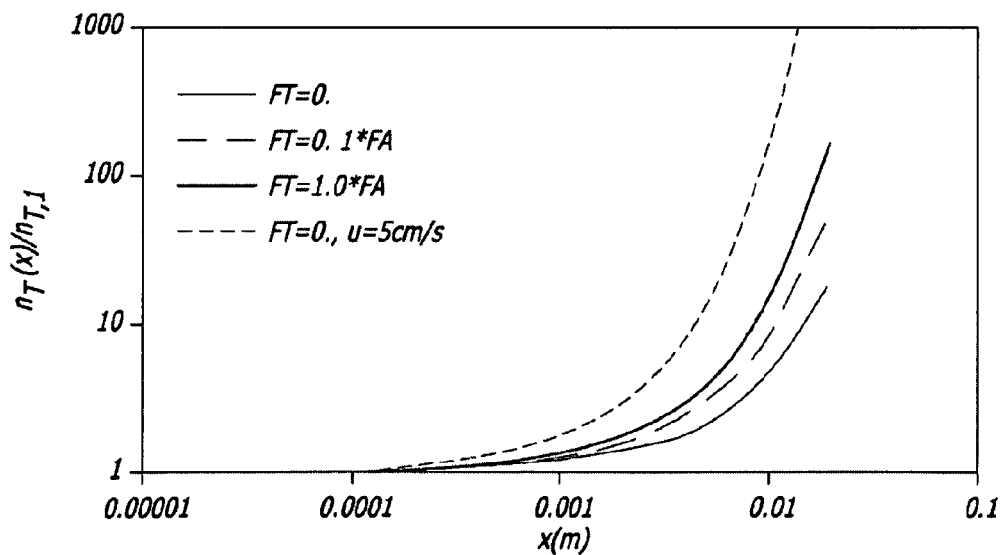

| Stage | Stage Length, L(cm) | Entrance, w(0) (cm) | Exit w(L) (μm) | Flow Speed, $U_{A,I}$ (cm/s) | τ (s) | V (mL/s) | Stage $\frac{n_{T,L}}{n_{T,I}}$ |
|---|---|---|---|---|---|---|---|
| 1 | 1 | 1 | $10^3$ | 10 | 0.1 | 0.1 | 10 |
| 2 | 0.33 | 0.33 | 330 | 3.3 | 0.1 | 0.01 | 10 |
| 3 | 0.1 | 0.1 | 100 | 1.0 | 0.1 | 0.001 | 10 |

FIG. 4

PRE-CONCENTRATOR FOR TRACE GAS ANALYSIS

CROSS REFERENCES TO RELATED APPLICATIONS

This application claims the benefit of priority under 35 U.S.C. §119(e) from co-pending, commonly owned U.S. provisional patent application Ser. No. 60/729,679, entitled "Quantum Separator—Continuous Micro and Meso Scale Pre-Concentration of Trace Molecules in Gases," filed on Oct. 24, 2005. The entire content of this provisional application is incorporated herein by reference.

BACKGROUND

Trace gas analyzers detect and analyze trace gases that have minute concentrations within a gas sample that typically includes a carrier gas or a diluent gas. Pre-concentrators may be used to increase the concentration of the trace gases within the gas samples to a level detectable by a detector.

Pre-concentrators that are based on adsorption membranes cannot operate on a continuous basis, because the gas must be stopped, a desired amount adsorbed, then released. These types of pre-concentrators may therefore not be able to maintain the time fidelity of the analyte gas concentrations.

Pre-concentrators that can operate continuously may be useful for detecting in substantial real time variations in the concentrations of the trace gases that are being analyzed.

SUMMARY

A pre-concentrator for analysis of a trace gas may include a flow channel and at least one separation membrane. The flow channel may have an inlet and an outlet, and may be configured to receive at the inlet a gas sample containing the trace gas and a carrier gas. The flow channel may have a width that decreases from the inlet to the outlet in such a way that the gas sample maintains a substantially constant flow speed through the flow channel. The flow channel may have a substantially constant height.

The separation membrane may define a portion of a side wall of the flow channel between the inlet and the outlet. The separation membrane may be configured to allow preferential removal of molecules of the carrier gas from the flow channel so as to increase concentration of the trace gas as the gas sample flows from the inlet to the outlet. The separation membrane may include a substantially non-adsorbing material that allows the gas sample to flow substantially continuously through the flow channel without being stopped by adsorption so that a variation in concentration of the trace gas within the gas sample can be detected in substantial real time.

A method in trace gas analysis is described of increasing concentration of a trace gas within a gas sample that includes the trace gas and a carrier gas. The method may include passing the gas sample at a substantially uniform flow speed through a pre-concentrator, causing the carrier gas to be preferentially removed from the gas sample through separation membranes that do not adsorb the carrier gas and the trace gas. In this way, the concentration of the trace gas within the gas sample may be raised to a level sufficient for detection of the trace gas by a detector.

BRIEF DESCRIPTION OF THE DRAWINGS

Following is a brief description of the drawings for the present disclosure. These drawings illustrate typical embodiments of the present disclosure, and are not to be considered limiting of the scope of the disclosure, which may admit to other equally effective embodiments. In the drawings, like reference numerals refer to the same or similar elements.

FIG. 2A illustrates a top view of the flow channel geometry.

FIG. 2B illustrates a side view of the flow channel geometry.

FIG. 3 illustrates the concentration of the trace gas molecules at a distance x from the inlet for a single concentration gas.

FIG. 4 is a table that illustrates the concentration stages for the multi-stage pre-concentrator system.

DETAILED DESCRIPTION

Continuously operating pre-concentrators for trace gas analysis are described. These pre-concentrators do not use adsorbing material, but are configured to raise the concentration of the analyte trace gas by causing the gas sample to preferentially lose the carrier gas through separation membranes. The pre-concentrators operate continuously without stopping the flow of the gases, so that variations in trace gas concentration can be tracked and detected in substantial real time. In one embodiment, the pre-concentrators may be operated in multiple stages to reach the desired detectable trace gas concentration.

Figure 1A:
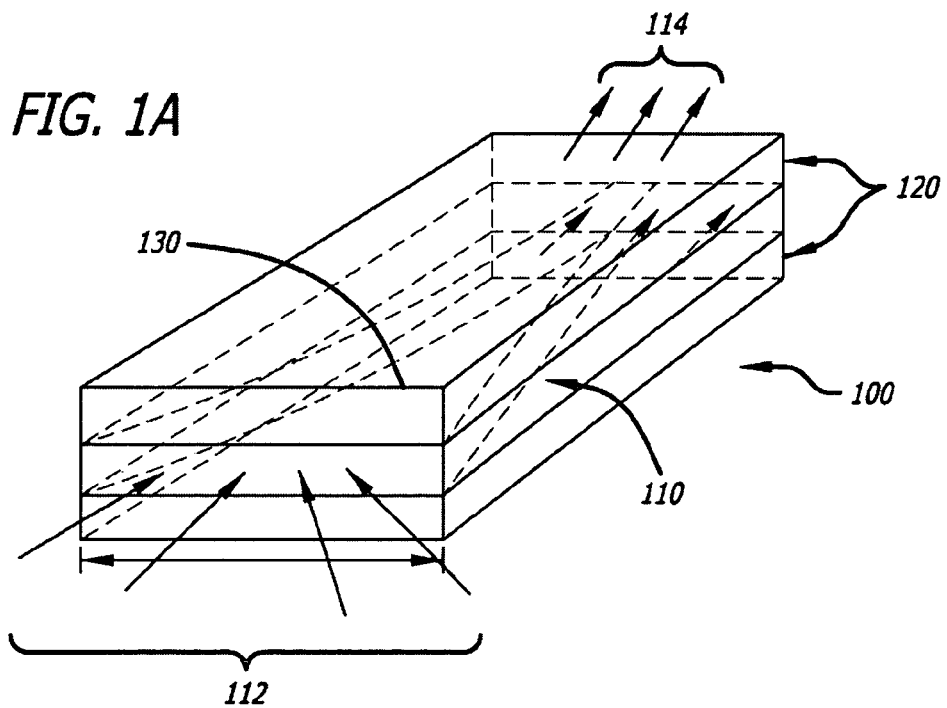
FIG. 1A is a schematic diagram of a pre-concentrator in accordance with one embodiment of the present disclosure.

FIG. 1A is a schematic diagram of a pre-concentrator 100 in accordance with one embodiment of the present disclosure. In overview, the pre-concentrator 100 includes a flow channel 110, at least one pumping chamber 120, and at least one separation membrane 130 between the flow channel 110 and each pump chamber 120. The separation membrane 130 defines at least a portion of the side wall of the flow channel 110.

Figure 1B:
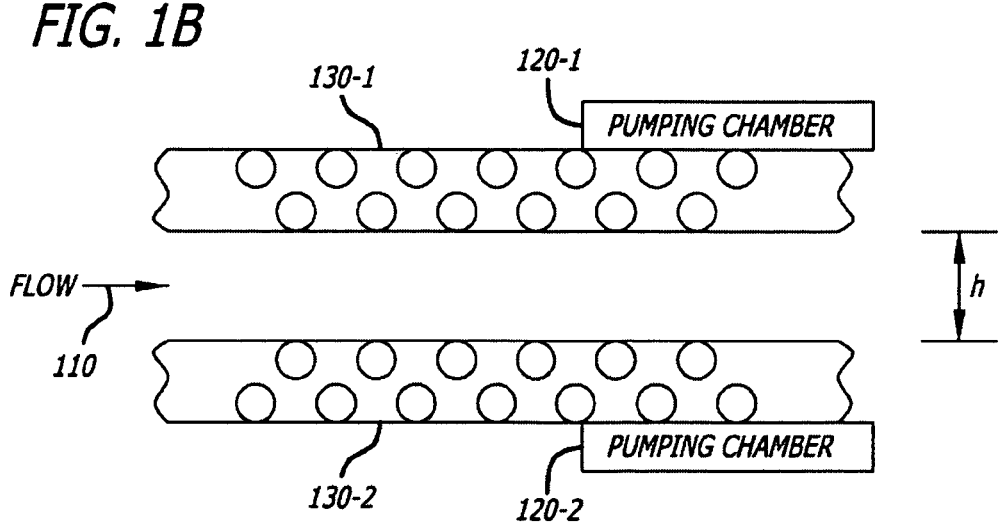
FIG. 1B illustrates an embodiment in which a first separation membrane and a second separation membrane are provided on respective side walls of the flow channel.

FIG. 1B illustrates an embodiment in which a first (upper) separation membrane 130-1 and a second (lower) separation membrane 130-2 are provided on one side wall and an opposite side wall of the flow channel 110, each separation membrane connected to a respective pump chamber 120-1 and 120-2. In the illustrated embodiment, the first separation membrane 130-1 defines a portion of a side wall of the flow channel 110, while the second separation membrane 130-2 defines a portion of an opposite side wall of the flow channel 110.

Although two pumping chambers have been shown in FIG. 1B for illustrative purposes, as a practical matter one pumping chamber should be used in order to provide the same low pressure environment at both of the separation membrane outlets. Using one pumping chamber would also cut down energy consumption. Different configurations of the membranes and the pumping chambers may be used, in different embodiments of the present disclosure.

Referring back to FIG. 1A, the flow channel 110 has an inlet 112 and an outlet 114, and is configured to receive at the inlet 112 a gas sample that contains both the trace gas (whose concentration is being detected), and a carrier (or diluent) gas. Typically, the flow channel is configured to receive at the inlet 112 a substantially continuous sampling of the gas sample. In the illustrated embodiment, the sampled gas is continuously drawn into the flow channel from the local atmosphere. The flow in the flow channel is kept to be in the continuum regime. In the illustrated embodiment, the sampled gas is overwhelmingly a carrier gas of number density $\eta_{A,i}$, with trace concentrations (1 to 1 E-3 ppb) of the trace gas (that is being analyzed) as molecules with number density $\eta_{T,i}$. The objective is to detect trace concentrations of the trace gas molecules.

Pre-concentration by the pre-concentrator 100 is performed by preferentially removing, through the separation membrane 130, molecules of the carrier gas from the flow channel 110, as the gas sample flows from the inlet 112 to the outlet 114. In other words, as the gas sample travels down the flow channel 110, the generally lighter and smaller carrier gas molecules preferentially diffuse through the separation membranes, escaping from the flow channel into the pumping chambers. In this way, concentration of the trace gas within the gas sample is increased.

The pumping chamber 120 creates and maintains a pressure difference across the separation membrane 130, i.e. between an inner surface of the separation membrane (connecting to the flow channel 110) and the upper surface of the separation membrane (connecting to the pumping chamber 130). In this way, the carrier gas molecules are preferentially diffused from the inner surface of the separation membrane 130 to the outer surface of the separation membrane 130 and into the pumping chamber 120, as the gas sample travels through the flow channel 100. The pressure difference may be a negative pressure gradient sufficient to maintain the substantially constant flow speed of the gas sample while overcoming viscous and other losses. The pumping chamber 120 may have a cross-sectional area that varies so as to maintain the pressure difference between the inner surface and the outer surface of the separation membrane and to thereby maintain the substantially constant flow speed of the gas sample in the flow channel.

A pump (not shown) may be connected to the pumping chamber, and may be operable to provide the requisite pressure difference at a desired volume flow of the gas sample through the flow channel.

The separation membrane 130 has a strength sufficient to withstand the pressure difference between its inner surface and its outer surface, and to maintain its shape substantially constant during the flow of the gas sample through the flow channel 110.

As a consequence of diffusive mass selection and/or size selection, the separation membrane 130 inhibits the trace gas molecules from passing through the channels within the separation membrane 130, while allowing the carrier gas molecules to pass more freely. In one embodiment, the channels of the separation membrane 130 may be capillary channels. In other embodiments of the present disclosure, separation membranes may be used that have non-capillary channels.

The separation membrane 130 is made of a substantially non-adsorbing material. This is in order to allow the gas sample to flow substantially continuously through the flow channel 110 without being stopped by adsorption. For the pre-concentrator 100 to work continuously for long periods, it is convenient if the trace gas molecules do not condense in the separation membrane channels due to the phenomenon of pore condensation. Thus, the rejection of these molecules from the separation membrane channels may be important.

In one embodiment, the separation membrane 130 may be a separation membrane that has been heated to improve the non-adsorbency of the separation membrane.

Because the gas sample flows substantially continuously, without being adsorbed and without pore condensation, the pre-concentrator 100 operates continuously. In this way, any variation in concentration of the trace gas within the gas sample that enters the inlet of 112 of the flow channel 110 can be detected in substantial real time at the outlet 114 of the flow channel 110.

The flow channel 110 has a constant height and a varying width, while the pumping chamber(s) 130 have constant widths and two dimensional, varying heights. FIG. 2A illustrates a top view of the flow channel geometry, while FIG. 2B illustrates a side view of the flow channel geometry. As seen from FIG. 2A, the flow channel 110 has a width that decreases from the inlet to the outlet in such a way that the trace gas and the carrier gas maintain a substantially constant flow speed through the flow channel 110. Pumping energy requirements can be minimized by having both the flow speed of the sampled gas and its number density remain essentially constant throughout the flow channel 110.

In some exemplary embodiments, the substantially constant height of the flow channel may be in the range of about 10 micrometers to about 1 millimeter, a length of about 100 micrometers to about 10 centimeters, and an inlet width of about 100 micrometers to about 10 centimeters, although other embodiments may have different ranges for the length, varying width, and height of the flow channel. In general, the flow channel height (shown as h in FIG. 2B), length (shown as L in FIG. 2A) and width (shown as W(x) in FIG. 2A) are typically designed according to the requirements of the particular trace gas analyzer for which the pre-concentrator is being used. For example, the particular type of trace gas molecule (which determines i.a. the molecular weight and size of the trace gas being analyzed), power budget, size constraint, separation membrane channel size, and the desired concentration of the trace gas molecules may have to be considered when determining the optimal size of the flow channel 110 in the pre-concentrator 100.

In addition to the varying width of the flow channel 110, an aerodynamic intake section upstream of the separation membrane channel may improve uniformity of the flow entering the flow channel, in both time and space coordinates.

In the pumping chamber(s) 120 backing the membranes, carrier gas number densities are a fraction $\eta$ of the number density at the entrance to the flow channel. The cross-sectional area of the pumping chamber(s), perpendicular to the x direction in the channel, can be adjusted by changing the height of the pumping chamber(s) according to the requirements of continuity. The result is both a constant average flow speed in the x direction and an approximately constant carrier gas number density throughout the pumping chamber(s).

For the analysis of the basic flow field of the pre-concentrator 100, concentrations of the trace gas molecules are so small that they have no influence on the flow dynamics in the flow channel 110. Once the flow field of the carrier gas is determined, the trace gas molecules are introduced by linear superposition.

In one embodiment, the separation membranes 130 can be modeled as a collection of a few tenths to ten nanometer internal diameter channels with relatively short lengths. In this embodiment, the separation membranes 130 are formed of arrays of nanometer diameter capillaries or apertures. The arrays are short enough to have relatively high transmissions or pumping speeds, and have an open area fraction of at least about 0.01. Also, the membranes must be strong enough to support the pressure differences created by the pump chambers.

When the array of capillaries have a diameter size of about several nanometers to several tens of nanometers, i.e. equal to or less than about one molecular mean free path relative to the gas sample in the flow channel, the preferential removal of the carrier gas molecules through the separation membrane 130 typically occurs by diffusive separation (also referred to as diffusive filtering). When the array of capillaries have a diameter size on the order of about one nanometer, the preferential removal of the carrier gas molecules through the separation membrane typically occurs by quantum separation (also referred to as quantum filtering) of the larger trace gas molecules, which are substantially prevented from passing through the separation membrane. When the array of capillaries have a diameter size in a sub-nanometer range, the preferential removal of the carrier gas molecules through the separation membrane typically occurs as a result of size separation (also referred to as size filtering, physical separation, or physical filtering) of the larger trace gas molecules which are substantially prevented from passing through the separation membrane.

An analysis of the carrier gas flow and the trace gas flow have been presented in the provisional application to which this patent application claims priority to, and which has been incorporated herein by reference.

FIG. 3 illustrates the resulting concentration of the trace gas molecules at a distance x from the inlet for a single concentration gas. The open area fraction for the trace gas molecules, $F_T$, is varied from 0, corresponding to effectively complete size separation, or quantum separation, of the trace gas molecules, to $F_A$, the same open area fraction as for the carrier gas molecules. For the latter case the concentration is provided only by the difference in mean thermal speeds of the carrier and trace gas molecules. For these results the carrier gas was assumed to be air and the trace gas (that is being targeted for analysis) had an assumed molecular weight MW=150. Unlike traditional gaseous diffusion separations, which use a lot of pumping energy, the approach here is to employ a relatively small pressure ratio of two or less.

For the data presented in FIG. 3, the pressure ratio, which is given by $(1/\eta_A)$, corresponded to $\eta_A=0.5$. For FIG. 3, a flow speed of 10 cm/s was selected. From FIG. 3 and at a distance of 1.5 cm it is possible to concentrate the trace gas molecules by a factor of 10 with no size separation or quantum separation, while the concentration increase is a factor of 100 at the same distance, with complete size or quantum separation.

The results presented above indicate the significant concentrations that potentially can be achieved by the pre-concentrator 100. While the results are most significant for the case of size separation, even the case of relatively massive trace gas molecules in air produces notable concentration increases.

In one embodiment, a multi-stage pre-concentrator system may be used in which the pre-concentrator works in multiple stages. In this embodiment, a plurality of pre-concentrators, as described above, are connected to each other so that concentration of the trace gas within a gas sample containing the trace gas and a carrier gas increases progressively as the gas sample flows through each one of the plurality of pre-concentrators in order.

In one embodiment, the plurality of pre-concentrators may be connected in series so as to gain a higher resulting concentration of the trace gas. In another embodiment, the plurality of pre-concentrators are connected in parallel so as to gain a higher resulting throughput of the trace gas.

FIG. 4 is a table that illustrates the concentration stages for the multi-stage pre-concentrator system, in which the concentration stages are put into a concentration cascade. There are a wide variety of ways to do this. No systematic study of optimizing possible concentration cascades has been completed. An example is presented in Table 1 for the case of $F_T=0$. The stage lengths and widths vary as indicated, flow speed is also varied as shown in Table 1. The three right hand columns give the sample transit time, volume flow, and concentration gain for each stage. In the embodiment described in conjunction with Table 1, the minimum dimension in each flow channel is no less than one hundred micrometers, in order to insure continuum flow. Many other possible configurations are possible.

The particular stage configurations chosen for the illustrative cascade of Table 1 provides a cascade concentration increase of 1E3 and a product volume flow of 0.001 mL/s at approximately atmospheric pressure. The sample transit time for the illustrative cascade is 0.3 sec.

A trace gas analyzer for analyzing a trace gas may include a single stage pre-concentrator, or a multi-stage pre-concentrator, both described above, as well as a detector (not shown) configured to detect concentration of the trace gas within the gas sample that exits an outlet of the flow channel.

In sum, continuously operating pre-concentrators for mobile and distributed trace gas analyzers have been described. Micro/meso-scale concentration cascades with one, two or more than two stages that potentially can provide trace gas concentration increases of a factor of 10 per stage, appear to be realistic.

While certain embodiments have been described of systems and methods for continuously operating pre-concentrators, it is to be understood that the concepts implicit in these embodiments may be used in other embodiments as well. The protection of this application is limited solely to the claims that now follow.

In these claims, reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference, and are intended to be encompassed by the claims. Moreover, nothing disclosed herein is intended to be dedicated to the public, regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A pre-concentrator for analysis of a trace gas, the pre-concentrator comprising:

a flow channel having an inlet and an outlet and configured to receive at the inlet a gas sample containing the trace gas and a carrier gas, the flow channel having a width that decreases from the inlet to the outlet in such a way that the gas sample maintains a substantially constant flow speed through the flow channel; and at least one separation membrane defining a portion of a side wall of the flow channel between the inlet and the outlet, the separation membrane configured to allow preferential removal of molecules of the carrier gas from the flow channel so as to increase concentration of the trace gas as the gas sample flows from the inlet to the outlet, the separation membrane including a substantially non-adsorbing material that allows the gas sample to flow substantially continuously through the flow channel without being stopped by adsorption so as to enable a variation in concentration of the trace gas within the gas sample to be detected in substantial real time.

2. The pre-concentrator of claim 1, further comprising:
at least one pumping chamber connected to the separation membrane and separated from the flow channel by the separation membrane, the pumping chamber configured to create and maintain a pressure difference between an inner surface of the membrane and an outer surface of the membrane so that the carrier gas molecules are preferentially diffused from the inner surface of the membrane to the outer surface of the membrane and into the pumping chamber and are thereby removed from the flow channel.

3. The pre-concentrator of claim 2, wherein the pumping chamber has a cross-sectional area that varies so as to maintain the pressure difference between the inner surface and the outer surface of the separation membrane and to thereby maintain the substantially constant flow speed of the gas sample in the flow channel.

4. The pre-concentrator of claim 2, wherein the separation membrane comprises a separation membrane that has been heated in order to improve non-adsorbency of the separation membrane.

5. The pre-concentrator of claim 2, wherein the separation membrane has a strength sufficient to withstand the pressure difference between the inner surface of the separation membrane and the outer surface of the separation membrane, and to maintain its shape substantially constant during the flow of the gas sample through the flow channel.

6. The pre-concentrator of claim 2, wherein the at least one separation membrane comprises:
a first separation membrane defining a portion of a side wall of the flow channel; and
a second separation membrane defining a portion of an opposite side wall of the flow channel.

7. The pre-concentrator of claim 6, wherein the at least one pumping chamber comprises:
a first pumping chamber connected to the first separation membrane; and
a second pumping chamber connected to the second separation membrane.

8. The pre-concentrator of claim 2, further comprising a pump connected to the pumping chamber, the pump operable to provide the pressure difference at a desired volume flow of the gas sample through the flow channel.

9. The pre-concentrator of claim 1, wherein the flow channel is configured to receive at the inlet a substantially continuous sampling of the gas sample containing the trace gas and the carrier gas.

10. The pre-concentrator of claim 1, wherein the flow channel has a substantially constant height.

11. The pre-concentrator of claim 10, wherein the substantially constant height of the flow channel is in the range of about 10 micrometers to about 1 millimeter.

12. The pre-concentrator of claim 1, wherein the flow channel has a substantially rectangular cross-section.

13. The pre-concentrator of claim 1, wherein the flow channel has a length of about 100 micrometers to about 10 centimeters.

14. The pre-concentrator of claim 1, wherein the flow channel has a width at the inlet of about 100 micrometers to about 10 centimeters.

15. The pre-concentrator of claim 1, wherein the separation membrane comprises an array of capillaries.

16. The pre-concentrator of claim 15, wherein the array of capillaries have a diameter size equal to or less than about one molecular mean free path relative to the gas sample in the flow channel, and wherein the preferential removal of the carrier gas molecules through the separation membrane occurs by diffusive separation.

17. The pre-concentrator of claim 15, wherein the array of capillaries have a diameter size in a sub-nanometer range, and wherein the preferential removal of the carrier gas molecules through the separation membrane occurs by size separation so that removal of the trace gas molecules from the flow channel is restricted.

18. The pre-concentrator of claim 15, wherein the array of capillaries have a diameter size on the order of about one nanometer, and wherein the preferential removal of the carrier gas molecules through the separation membrane occurs by quantum separation.

19. The pre-concentrator of claim 1, wherein the separation membrane has an open area fraction greater than about 0.01.

20. A multi-stage pre-concentrator system for analysis of a trace gas, comprising:
a plurality of pre-concentrators connected to each other so that concentration of the trace gas within a gas sample containing the trace gas and a carrier gas increases progressively as the gas sample flows through each one of the plurality of pre-concentrators in order;
wherein each pre-concentrator comprises:
a flow channel having an inlet and an outlet and configured to receive at the inlet a gas sample containing the trace gas and a carrier gas, the flow channel having a width that decreases from the inlet to the outlet in such a way that the trace gas and the carrier gas maintain a substantially constant flow speed through the flow channel; and
at least one separation membrane defining a portion of a side wall of the flow channel between the inlet and the outlet, the separation membrane configured to allow preferential removal of molecules of the carrier gas from the flow channel so as to increase concentration of the trace gas as the gas sample flows from the inlet to the outlet, the separation membrane including a substantially non-adsorbing material that allows the gas sample to flow substantially continuously through the flow channel without being stopped by adsorption so as to enable a variation in concentration of the trace gas within the gas sample to be detected in substantial real time.

21. The multi-stage pre-concentrator system of claim 20, wherein the plurality of pre-concentrators are connected in series so as to gain a higher resulting concentration of the trace gas.

22. The multi-stage pre-concentrator system of claim 20, wherein the plurality of pre-concentrators are connected in parallel so as to gain a higher resulting throughput of the trace gas.

23. A trace gas analyzer for analyzing a trace gas, the trace gas analyzer comprising:
at least one pre-concentrator configured to increase concentration of the trace gas within a gas sample that includes the trace gas and a carrier gas, as the gas sample flows through a flow channel within the pre-concentrator; and
a detector configured to detect concentration of the trace gas within the gas sample that exits an outlet of the flow channel;
wherein the at least one pre-concentrator comprises:
a flow channel having an inlet and an outlet and configured to receive at the inlet a gas sample containing the trace gas and a carrier gas the flow channel having a width that decreases from the inlet to the outlet in such a way that the trace gas and the carrier gas maintain a substantially constant flow speed through the flow channel; and at least one separation membrane defining a portion of a side wall of the flow channel between the inlet and the outlet, the separation membrane configured to allow preferential removal of molecules of the carrier gas from the flow channel so as to increase concentration of the trace gas as the gas sample flows from the inlet to the outlet, the separation membrane including a substantially non-adsorbing material that allows the gas sample to flow substantially continuously through the flow channel without being stopped by adsorption so as to enable a variation in concentration of the trace gas within the gas sample to be detected in substantial real time.

24. The trace gas analyzer of claim 23, wherein the at least one pre-concentrator comprises a plurality of pre-concentrators connected to each other so that concentration of the trace gas within a gas sample containing the trace gas and a carrier gas increases progressively as the gas sample flows through each one of the plurality of pre-concentrators.

* * * * *